US011219402B2

(12) United States Patent
Port et al.

(10) Patent No.: US 11,219,402 B2
(45) Date of Patent: Jan. 11, 2022

(54) SYSTEMS AND METHODS FOR PRODUCING IMAGING BIOMARKERS INDICATIVE OF A NEUROLOGICAL DISEASE STATE USING GRAY MATTER SUPPRESSIONS VIA DOUBLE INVERSION-RECOVERY MAGNETIC RESONANCE IMAGING

(71) Applicant: MAYO FOUNDATION FOR MEDICAL EDUCATION AND RESEARCH, Rochester, MN (US)

(72) Inventors: John D. Port, Rochester, MN (US); Istvan Pirko, Rochester, MN (US); Jan-Mendelt Tillema, Anstelveen (NL); Yunhong Shu, Rochester, MN (US); Claudia F. Lucchinetti, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1463 days.

(21) Appl. No.: 15/022,404

(22) PCT Filed: Sep. 22, 2014

(86) PCT No.: PCT/US2014/056762
§ 371 (c)(1),
(2) Date: Mar. 16, 2016

(87) PCT Pub. No.: WO2015/042519
PCT Pub. Date: Mar. 26, 2015

(65) Prior Publication Data
US 2016/0220168 A1 Aug. 4, 2016

Related U.S. Application Data

(60) Provisional application No. 61/880,386, filed on Sep. 20, 2013.

(51) Int. Cl.
*A61B 5/00* (2006.01)
*A61B 5/055* (2006.01)
(Continued)

(52) U.S. Cl.
CPC .......... *A61B 5/4076* (2013.01); *A61B 5/0042* (2013.01); *A61B 5/055* (2013.01);
(Continued)

(58) Field of Classification Search
CPC .................................................... A61B 5/0042
See application file for complete search history.

(56) References Cited

U.S. PATENT DOCUMENTS 9,063,206 B2 * 6/2015 Madhuranthakam ........................
G01R 33/5602
2005/0273017 A1 * 12/2005 Gordon ................ A61B 5/4088
600/544

(Continued)

FOREIGN PATENT DOCUMENTS

WO   WO-2011044442 A1 *  4/2011  ............. A61B 6/037
WO       2013/103791 A1     7/2013

OTHER PUBLICATIONS

International Search Report and Written Opinion under dated Mar. 20, 2015 in connection with PCT/US2014/056762.

*Primary Examiner* — Rochelle D Turchen
(74) *Attorney, Agent, or Firm* — Quarles & Brady LLP (57) ABSTRACT

Systems and methods related to imaging biomarkers for determining neurological disease states of a subject are provided. In one embodiment, a method for producing an image indicative of a neurological disease using a magnetic resonance imaging ("MRI") system is provided. The method includes directing the MRI system to perform a double inversion-recovery ("DIR") pulse sequence to generate data where signals from gray matter and cerebral spinal fluid are
(Continued)

substantially suppressed. The method also includes analyzing the DIR images, reconstructed from the acquired data, to identify cortical and white matter lesions. This includes identifying imaging biomarkers based on visual signatures of brain tissue, including white matter tissue. In some aspects, diffusion-weighted data may also be obtained using the MRI system. Diffusion-weighted data may be used in a tractography process to determine connectivities, or connectivity patterns between the identified lesions, including cortical lesions, to determine neurological disease states of the subject.

9 Claims, 7 Drawing Sheets

(51) Int. Cl.
*G01R 33/56* (2006.01)
*G01R 33/563* (2006.01)

(52) U.S. Cl.
CPC ..... *G01R 33/5602* (2013.01); *G01R 33/5608* (2013.01); *G01R 33/56341* (2013.01); *A61B 2576/026* (2013.01)

(56) References Cited

U.S. PATENT DOCUMENTS

| | | |
|---|---|---|
| 2007/0249929 A1 | 10/2007 | Jeong et al. |
| 2008/0205733 A1 | 8/2008 | Laidlaw et al. |
| 2010/0215239 A1 | 8/2010 | Assaf |
| 2010/0278408 A1 | 11/2010 | Wiemker et al. |
| 2013/0178693 A1 | 7/2013 | Neuvonen et al. |
| 2014/0347051 A1* | 11/2014 | Kecskemeti ....... G01R 33/5602 324/309 |
| 2015/0302599 A1* | 10/2015 | Crainiceanu ........... G01R 33/50 382/131 |

* cited by examiner

SYSTEMS AND METHODS FOR PRODUCING IMAGING BIOMARKERS INDICATIVE OF A NEUROLOGICAL DISEASE STATE USING GRAY MATTER SUPPRESSIONS VIA DOUBLE INVERSION-RECOVERY MAGNETIC RESONANCE IMAGING

CROSS-REFERENCE TO RELATED APPLICATIONS

This application represents the national stage entry of PCT International Application No. PCT/US2014/056762 filed Sep. 22, 2014, which claims priority to, U.S. Provisional Application Ser. No. 61/880,386, filed Sep. 20, 2013, both of which are hereby incorporated herein by reference for all purposes.

STATEMENT REGARDING FEDERALLY SPONSORED RESEARCH

N/A

BACKGROUND OF THE INVENTION

The field of the present invention is magnetic resonance imaging ("MRI") methods and systems. More particularly, the present invention relates to systems methods for identifying or diagnosing multiple sclerosis ("MS") and other neurological disorders, or individuals at risk of getting MS or other neurological disorders. Furthermore, the present invention relates to quantitative measurement of appearance and connectivity of cerebral tissues on MR images as biomarkers for MS and other neurological disorders.

Multiple sclerosis is an idiopathic inflammatory demyelinating disease, with the hallmark of demyelinated white matter lesions ("WML"). Through major advances in neuropathology and imaging research, it is now well accepted that there is a significant cortical pathology and cortical lesion ("CL") formation in MS, which becomes most prominent in progressive MS. In severe cases, confluent cortical demyelination can span multiple gyri. In addition, cortical demyelination is also present in the earliest stages of MS, and the acute stage of CL formation is highly inflammatory.

In general practice, MRI is the main imaging modality for detection of focal and diffuse abnormalities in the brain of MS patients due its to superior soft tissue sensitivity. Specifically, standard MR techniques are restricted to imaging proton density ("PD"), $T_1$ and $T_2$ signal contrast behavior of MS lesions. However, such conventional techniques are limited and typically fail to capture the extent of cortical pathology in MS. For instance, histopathological studies have demonstrated that microscopic abnormalities may be present both in white matter ("WM") and gray matter ("GM") and appear normal on standard MR images.

Some studies have attempted to utilize double inversion recovery ("DIR") imaging techniques to improve detection of MS lesions. Generally, DIR sequences allow selective imaging of GM tissues by nulling magnetic resonance signals from normal WM and cerebral spinal fluid ("CSF"). However, such sequences have intrinsically low signal-to-noise ratio ("SNR"), and hence in addition to careful adaptation of pulse parameters and saturation techniques, improved CL detection necessitated higher magnetic field values. Similarly, sensitive CL detection was also accomplished by using T2*-weighted sequences at magnetic fields strengths of 7 Tesla.

However, application of high field strengths to patients is currently not approved for clinical use. In addition, results achieved with standard DIR imaging techniques that are commercially and clinically available are still inferior when compared to standard histopathology. In particular, suppression of normal-appearing WM and CSF in DIR imaging produces poor sensitivity in identifying subpial plaques, which are the most common cortical lesions observed in early MS and clinically isolated syndrome ("CIS") cases.

Hence, the discrepancy between conventional MRI findings, histopathological data and functional outcomes underscores a necessity for improved MRI methods for assessing disease burden. Specifically, there is a need for non-invasive imaging techniques capable of increased sensitivity to abnormalities associated with MS, for example, cortical plaques, that are clinically available on standard scanners, and operate at FDA-approved magnetic fields strengths. In addition, there is a need for new approaches to analyzing identified abnormalities in order to reveal underlying relationships and indicators of neurological diseases.

SUMMARY OF THE INVENTION

The present invention overcomes the aforementioned drawbacks by providing systems and methods directed to producing and utilizing imaging biomarkers indicative of a neurological disease, such as multiple sclerosis ("MS"). Specifically, using gray matter ("GM") and cerebral spinal fluid ("CSF") suppression in double inversion-recovery ("DIR") magnetic resonance imaging ("MRI"), the conspicuity and connectivity of abnormal lesions, including cortical lesions ("CL"), may be determined.

As will be described, a determined connectivity associated with certain abnormal lesions, in accordance with aspects of the present disclosure, may be used as a biomarker of disease states, including stages of progression and/or at-risk pathways of pathology. For example, a topographical association between meningeal inflammation, cortical demyelination and underlying white matter pathology may be determined for diagnosing MS. In addition, lesions appearing on images acquired in accordance with the present disclosure, and identified by their unique visual marks, signature and anatomical location, can be used as indicators of neurological disease states. For example, lesions appearing on GM suppressed DIR images, to include hypointense or hyperintense central regions, which may be non-uniform, surrounded by hypointense rims or rings, may be used as biomarkers for MS.

In one aspect of the present disclosure, a method for producing an image indicative of a neurological disease state of a subject using a magnetic resonance imaging ("MRI") system is provided. The method includes directing the MRI system to acquire data by performing a double inversion recovery pulse sequence that selectively nulls magnetic resonance signals originating from gray matter and cerebrospinal fluid, and directing the MRI system to acquire diffusion-weighted data by performing a diffusion-weighted pulse sequence. The method also includes reconstructing a set of images from the data, including a set of diffusion-weighted images from the data. The method further includes identifying in the set images at least one region-of-interest representing at least one cortical lesion and at least one region-of-interest representing at least one white matter lesion, and producing an image indicative of a connectivity between the at least one cortical lesion and the at least one white matter lesion using the set of diffusion-weighted images and the regions-of-interest identified.

In another aspect of the present disclosure, a method for determining a neurological disease state using a magnetic resonance imaging ("MRI") system is provided. The method includes directing the MRI system to acquire data from a subject by performing a double inversion recovery pulse sequence that selectively nulls magnetic resonance signals originating from gray matter and cerebrospinal fluid, and reconstructing a set of images from the acquired data. The method also includes identifying an imaging biomarker by analyzing the set of images for a visual signature of white matter tissue, and determining a neurological disease state using the identified imaging biomarker.

In yet another aspect of the present disclosure, a magnetic resonance imaging ("MRI") system is provided. The MRI system includes a magnet system configured to generate a polarizing magnetic field about at least a portion of a subject arranged in the MRI system, a plurality of gradient coils configured to apply a gradient field to the polarizing magnetic field, and a radio frequency ("RF") system configured to apply a RF excitation field to a region of interest in the subject and acquire MR image data therefrom. The MRI system also includes a computer system programmed to perform a double inversion recovery pulse sequence that selectively nulls magnetic resonance signals originating from gray matter and cerebrospinal fluid by controlling the magnet system, gradient coils and RF system, and acquire signal data generated using the double inversion recovery pulse sequence. The computer system is also configured to reconstruct a set of images from the acquired signal data, and identify an imaging biomarker by analyzing the set of images for a visual signature of brain tissue. The computer system is further configured to determine a neurological disease state using the identified imaging biomarker.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Double inversion recovery ("DIR") pulse sequences in neuroimaging applications of MRI can be used to enhance the conspicuity of certain types of brain lesions by implementing two inversion recovery ("IR") radio frequency ("RF") pulses that are timed to suppress two different types of tissues. Conventional DIR sequences target the suppression of normal white matter ("WM") and cerebral spinal fluid ("CSF") signals and generate images referred to herein as WM-DIR images.

It is a discovery of the present invention, however, and contrary to conventional practice, that using a DIR pulse sequence that is configured to suppress normal cortical gray matter ("GM") and CSF, instead of WM, can provide unique information pertaining to disease states and progression. Specifically, this information forms the basis of one or more imaging biomarkers that can be used to diagnose neurological diseases, such as multiple sclerosis. Such a pulse sequence is referred herein as a "GM-DIR" pulse sequence and images generated therefrom are GM-DIR images. For example, in some aspects, an imaging biomarker includes the visual signature of certain lesions visible on GM-DIR images that may not be present, or may appear different, in traditional DIR images in which WM and CSF are suppressed.

Figure 1:
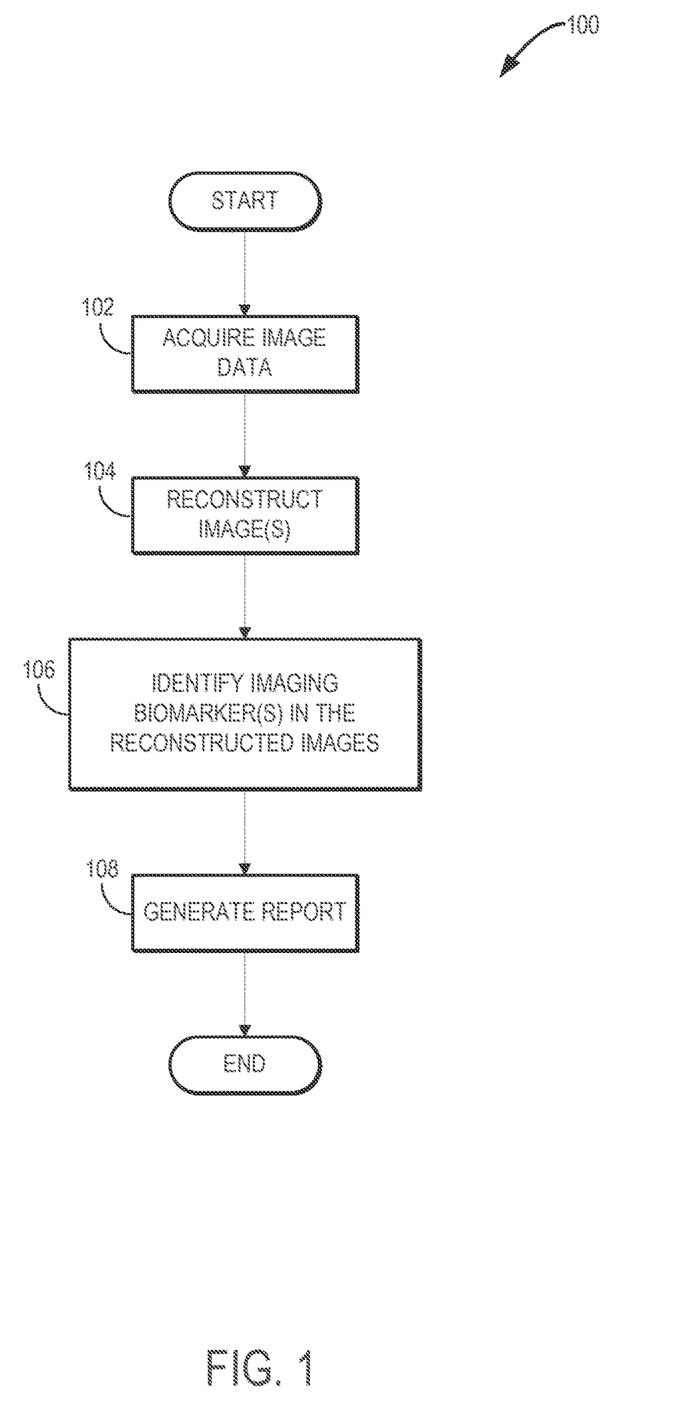
FIG. 1 is a flowchart illustrating a steps in process of determining neurological disease states of a subject in accordance with the present disclosure.

Referring now to FIG. 1, a flowchart setting forth the steps of a process 100 for producing images, including GM-DIR images, and analyzing those images for biomarkers that indicate particular neurological disease states is illustrated. The process 100 begins with the acquisition of MRI data, as indicated at step 102, whereby an MRI system may be directed to acquire data from a subject by performing a double inversion recovery pulse sequence that selectively nulls magnetic resonance signals originating from gray matter and cerebrospinal fluid. An example of such a pulse sequence is provided below. As described, this approach allows more specific radiological identification of MS lesions, such as cortical lesions, compared to standard DIR imaging techniques. However, other image data can also be acquired at step 102 using the MRI system, including standard DIR data with WM and CSF suppression, diffusion-weighted data, $T_1$-weighted data, $T_2$-weighted data, $T_2^*$-weighted data and so on. Additionally, other image data can be acquired using other imaging modalities.

From the acquired data, various sets of images may be reconstructed, as indicated at step 104. Once reconstructed, at step 106, the sets of images may then be autonomously or non-autonomously processed, using any system or systems configured to do, to identify indicators or biomarkers of disease. Specifically, one or more imaging biomarkers may be produced or identified by analyzing specific sets of reconstructed images, including GM-DIR images, regions-of-interest identified in such images, regions-of-interest segmented from such images, or combinations thereof. Conceivably, information from all of the reconstructed image sets may be combined to determine or identify multiple markers or indicators related to disease states, such as cortical or other brain lesions. As an example, combining information from the reconstructed image sets may include segmenting, registering, overlaying, or combinations thereof, images, structures-of-interest in the images, or specific features in the images, In some aspects, image markers or visual signatures, anatomical locations, and other characteristics, may be analyzed on the sets of reconstructed or combined images to identify tissues or structures associated with normal or abnormal brain tissues, such as white matter and/or gray matter tissues or lesions. For example, an analyzed visual signature can include lesions appearing on GM-DIR images as heterogeneous pixel patterns of hypo or hyperintense areas having pixel regions surrounded, partially or fully, by hypointense rings, rims, halos, or other boundaries.

Figure 5:
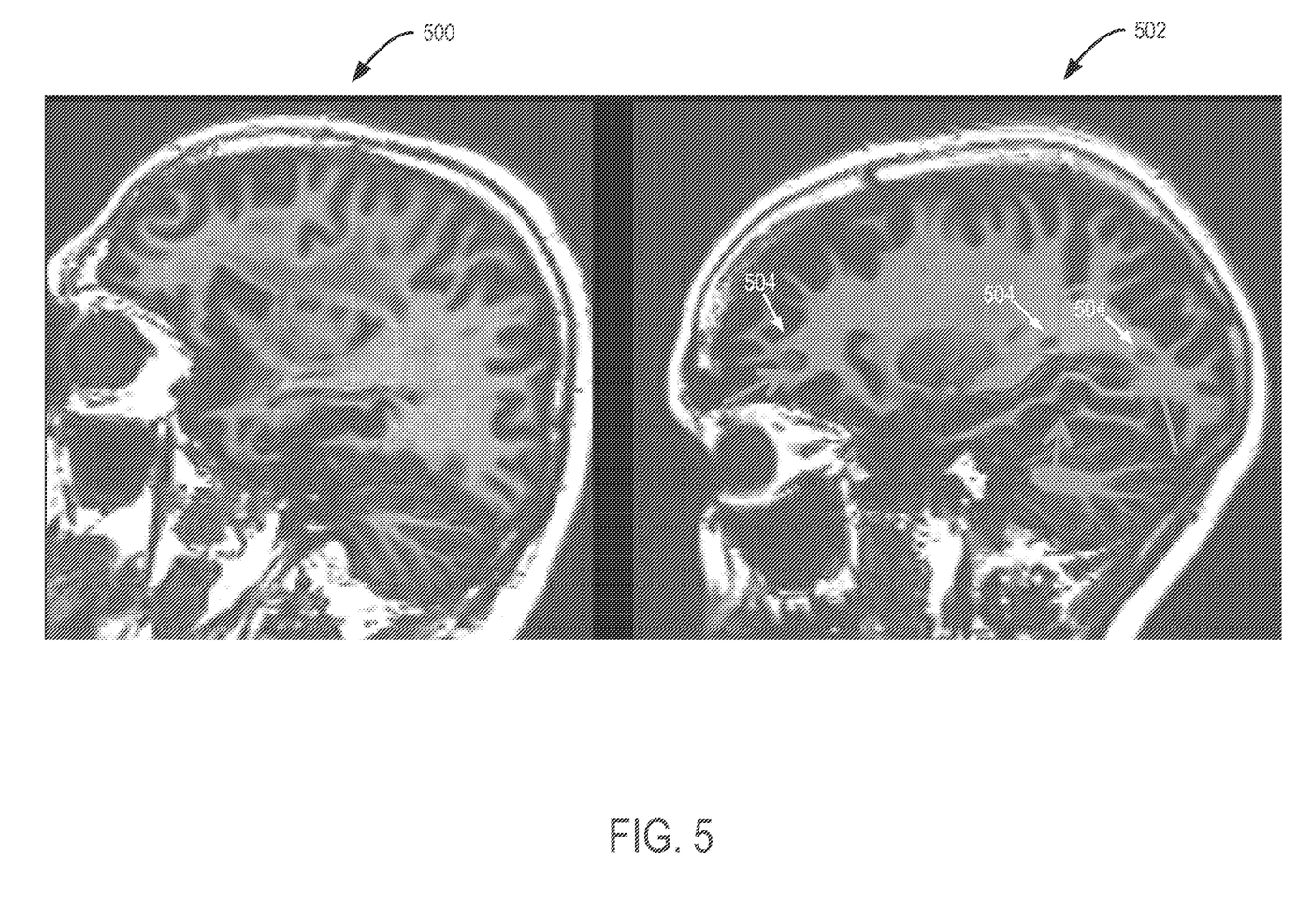
FIG. 5 shows images illustrating specificity to multiple sclerosis ("MS") of lesional appearance on gray matter double-inversion recovery ("GM-DIR") images.

By way of example, the potential specificity to MS of lesional appearance on GM-DIR images is illustrated in two scans shown in FIG. 5 Namely, the first image 500 is of a patient with non-specific small vessel ischemic white matter lesions, and the second image 502 is of an MS case. Markers 504 on the second image 502 indicate the "MS-specific" lesion appearance on GM-DIR, whereas the lesions in the small vessels ischemic disease-case show uniform lesional hypointensity without dark rims and heterogeneous centers.

In other aspects, additional images, maps or representations may be generated at step 106 using reconstructed or combined images or representations. For instance, images indicative of connectivity between identified cortical lesions and white matter lesions may be produced. Specifically, using reconstructed diffusion-weighted images, a probabilistic tractography process may be performed, in which identified lesions, including cortical lesions and white matter lesions, may be used as seed locations. In some aspects, lesion connectivity, and/or metrics associated with lesion connectivity, may be determined using tracts from each individual seed lesion, and identified WM lesions and/or cortical lesions in each tract.

Using visual signatures, connectivity metrics, or both identified using GM-DIR images and other images as biomarkers for neurological disease, a report may be generated, as indicated at step 108. Such a report may be in any suitable form, and can include information or indications related to neurological disease states, disease progressions, tumor burdens, or effects resulting from treatment. For example, the report may indicate whether the subject has a positive diagnosis of MS.

In some aspects, the report may include displays of raw or processed images, structure maps, overlays, metrics, and other information. For example, information may be provided in relation to a percentage of lesions that connect from WM lesions to other WM lesions (WML-WML), WM lesions to cortical lesions (WML-CL) and cortical lesions to WM lesions (CL-WML). In another example, binary maps may also be displayed as connected/non-connected cortex maps.

Figure 2:
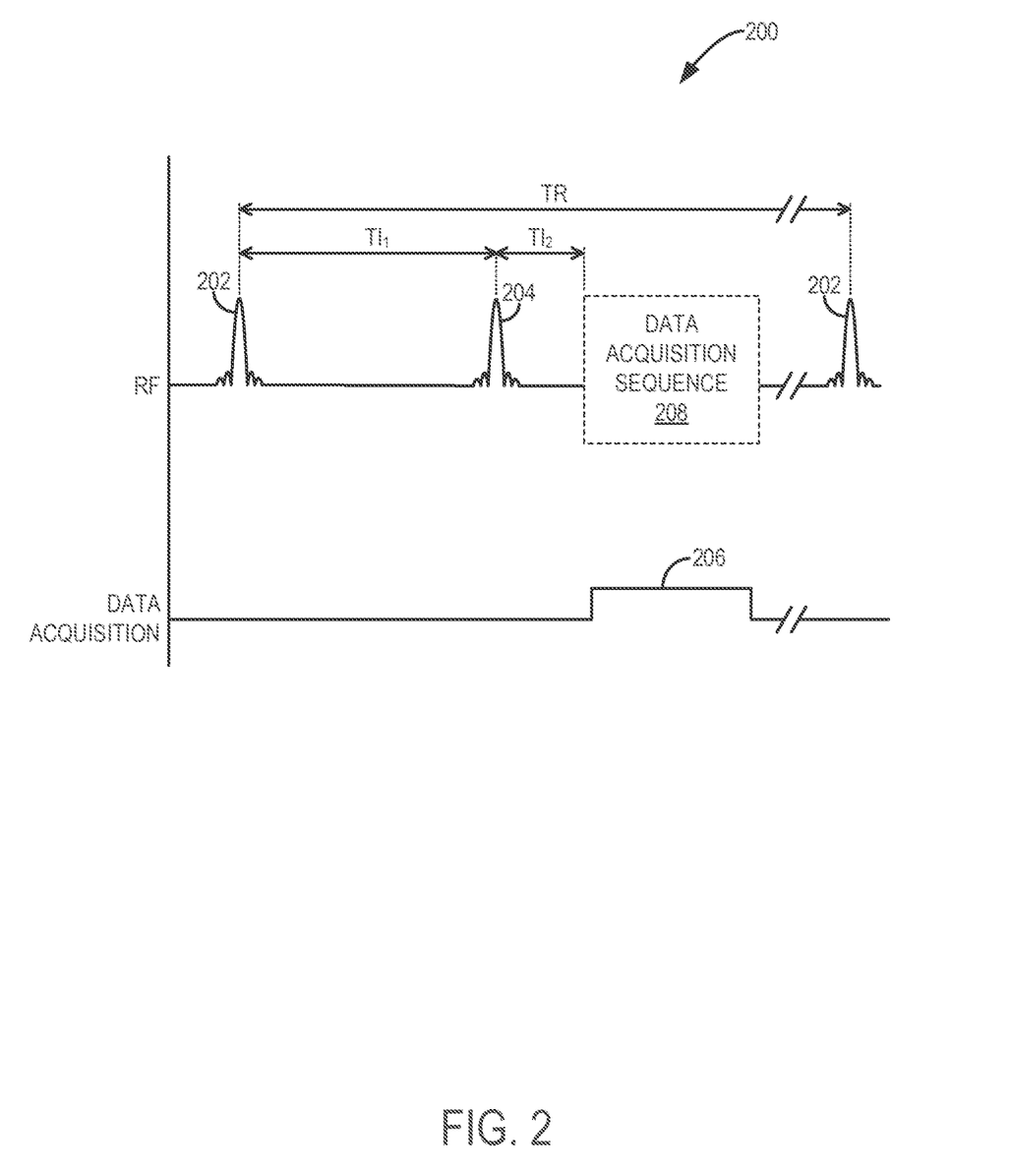
FIG. 2 is a pulse sequence showing a dual inversion recovery sequence for use in accordance with aspects of the present disclosure.

Referring now to FIG. 2, an example of a pulse sequence 200 for acquiring DIR images in which GM and CSF are suppressed is illustrated. In this example, the pulse sequence includes a first inversion recovery RF pulse 202 followed by a second IR RF pulse 204. By way of example, both IR RF pulses 202, 204 are designed to rotate longitudinal magnetization by a flip angle, β. The flip angle is preferably at or near 180 degrees; however, it will be appreciated that other flip angles can also be used depending on the imaging application at task, the desired effect on longitudinal magnetization, and considerations for optimizing total scan time. In some instances, the IR RF pulses 202, 204 can have different flip angles, $β_1$ and $β_2$. The first and second IR RF pulses 202, 204 are separated in time by a first inversion time, $TI_1$.

After application of the second IR RF pulse 204, data is acquired from the subject being imaged, as indicated by data acquisition block 206. Data acquisition commences with the performance of a data acquisition sequence 208. By way of example, the data acquisition sequence 208 may include a fast spin echo type of pulse sequence, although other acquisition sequences may be readily substituted as desired. The second IR RF pulse 204 and the beginning of the data acquisition sequence 208 are separated in time by a second inversion time, $TI_2$. Specifically, selection of $TI_1$ and $TI_2$ for the DIR sequence may be chosen such that signals from two different tissue types, for example GM and CSF, are substantially nulled. As is routine in the art, the pulse sequence 200 can be repeated in successive repetition time ("TR") intervals until the desired amount of data has been acquired.

Visualization of topographical connections between elements associated with MS, including meningeal inflammation, cortical demyelination, and underlying WM pathology, may have important ramifications in MS pathogenesis, as well as diagnostic, prognostic and treatment implications. Diffusion tensor imaging ("DTI")-based probabilistic tractography is a method that enables visualization of subtle pathology by quantitatively assessing WM tracts and providing sensitive measures of WM integrity, such as fractional anisotropy and diffusivity. Combining brain lesion information obtained from the increased sensitivity of DIR pulse sequence imaging, in accordance with aspects of the present disclosure, and perhaps other complementary images, with connectivity information from DTI may identify key factors driving early as well as chronic MS disease.

From histological studies performed by the inventors, it is contemplated that white matter lesions (WMLs) form in areas directly connected with cortical gray matter plaques. In other words, the locations of CLs determine the location of WMLs. This discovery can provide a unique imaging biomarker for multiple sclerosis. As will be described below, this connectivity can be measured using imaging methods that are sensitive to CL detection in combination with diffusion tensor imaging-based probabilistic tractography.

Figure 3:
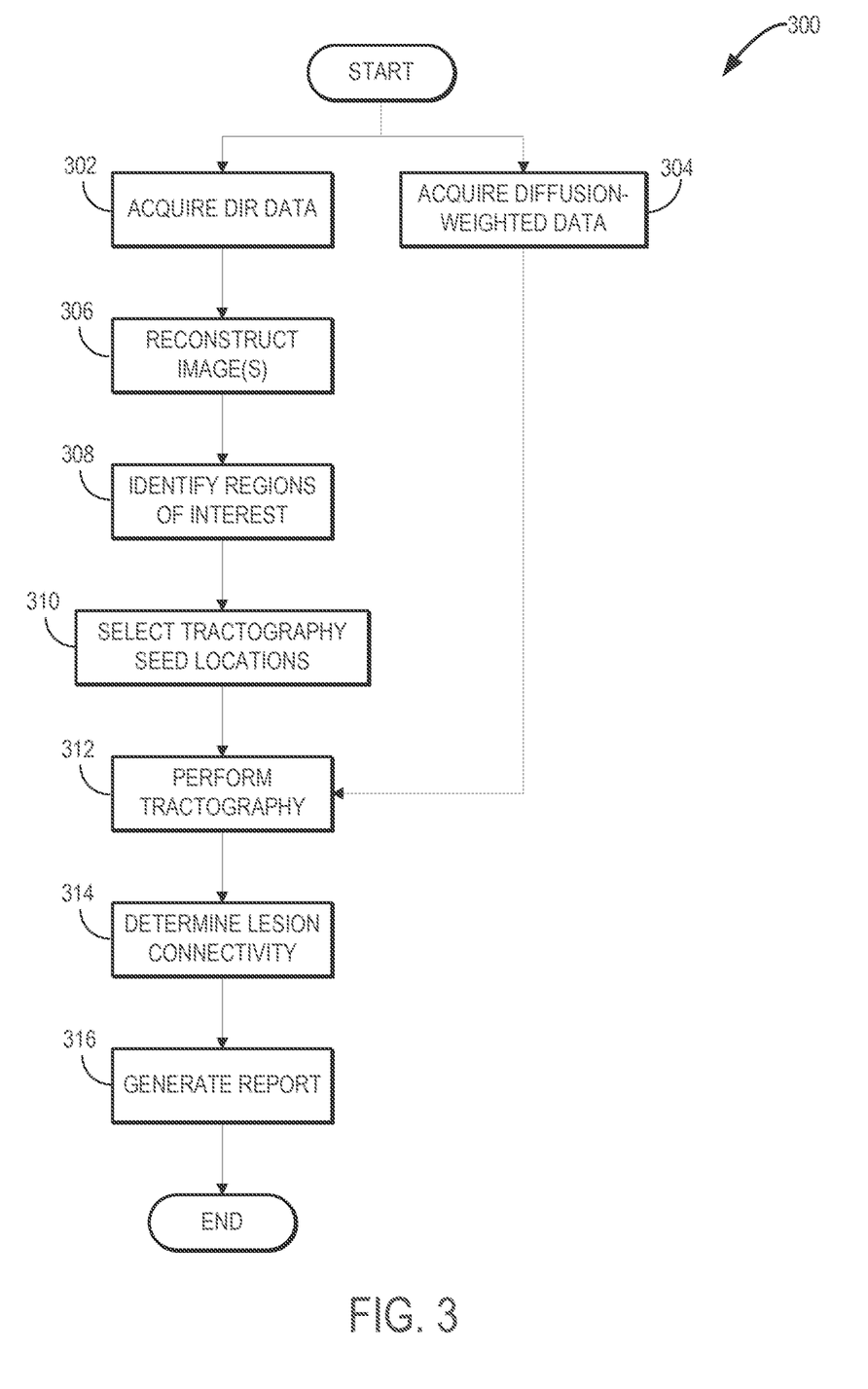
FIG. 3 is a flowchart illustrating a technique for determining lesion connectivity for use in accordance with aspects of the present disclosure.

Referring to FIG. 3, a flowchart 300 is shown illustrating the steps involved in a method for determining the connectivity between regions of interest identified in DIR imaging. In this method, DIR data 302 and diffusion-weighted data 304 are acquired using a series of DIR pulse sequences and diffusion-weighted pulse sequences, respectively. In some aspects, data acquisition steps 302 and 304 may be carried out in a manner that optimizes scan time and/or image quality. After a number of various pre-processing steps, the DIR data is reconstructed 306 into images. Regions of interest that are consistent with GM and WM brain lesions are then identified in these images, as indicated at step 308. Once various WM and/or GM seed lesion locations are selected 310, a tractography method is performed at step 312, in which connective pathways are determined between the seeds and other lesion locations. Once lesion connectivity has been identified for each selected seed, as indicated at step 314, a report is generated, as indicated at step 316. This report may take the form of various quantitative metrics, indicators, and outputs. In some aspects, an indication related to disease states, disease progressions, tumor burdens, or effects resulting from treatment may be provided in the report.

Figure 4:
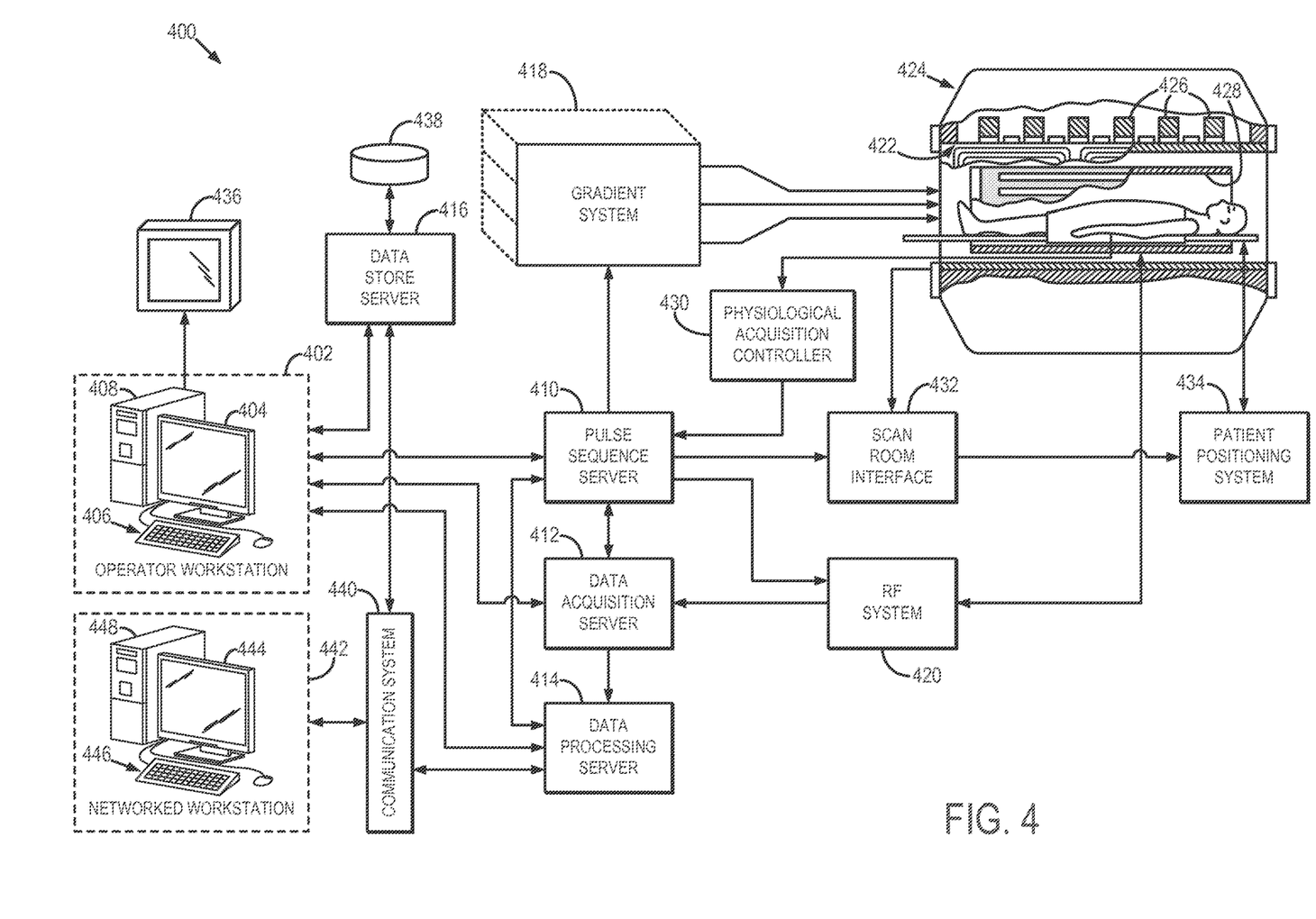
FIG. 4 is a schematic block diagram of an exemplary MR imaging system for use in accordance with the present disclosure.

Referring particularly now to FIG. 4, an example of a magnetic resonance imaging ("MRI") system 400 is illustrated. The MRI system 400 includes an operator workstation 402, which will typically include a display 404; one or more input devices 406, such as a keyboard and mouse; and a processor 408. The processor 408 may include a commercially available programmable machine running a commercially available operating system. The operator workstation 402 provides the operator interface that enables scan prescriptions to be entered into the MRI system 400. In general, the operator workstation 402 may be coupled to four servers: a pulse sequence server 410; a data acquisition server 412; a data processing server 414; and a data store server 416. The operator workstation 402 and each server 410, 412, 414, and 416 are connected to communicate with each other. For example, the servers 410, 412, 414, and 416 may be connected via a communication system 440, which may include any suitable network connection, whether wired, wireless, or a combination of both. As an example, the communication system 440 may include both proprietary or dedicated networks, as well as open networks, such as the internet.

The pulse sequence server 410 functions in response to instructions downloaded from the operator workstation 402 to operate a gradient system 418 and a radiofrequency ("RF") system 420. Gradient waveforms necessary to perform the prescribed scan are produced and applied to the gradient system 418, which excites gradient coils in an assembly 422 to produce the magnetic field gradients $G_x$, $G_y$, and $G_z$ used for position encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil (not shown in FIG. 4), in order to perform the prescribed magnetic resonance pulse sequence. Responsive magnetic resonance signals detected by the RF coil 428, or a separate local coil (not shown in FIG. 4), are received by the RF system 420, where they are amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the scan prescription and direction from the pulse sequence server 410 to produce RF pulses of the desired frequency, phase, and pulse amplitude waveform. The generated RF pulses may be applied to the whole-body RF coil 428 or to one or more local coils or coil arrays (not shown in FIG. 4).

The RF system 420 also includes one or more RF receiver channels. Each RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 410 also optionally receives patient data from a physiological acquisition controller 430. By way of example, the physiological acquisition controller 430 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 410 to synchronize, or "gate," the performance of the scan with the subject's heart beat or respiration.

The pulse sequence server 410 also connects to a scan room interface circuit 432 that receives signals from various sensors associated with the condition of the patient and the magnet system. It is also through the scan room interface circuit 432 that a patient positioning system 434 receives commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, such that no data is lost by data overrun. In some scans, the data acquisition server 412 does little more than pass the acquired magnetic resonance data to the data processor server 414. However, in scans that require information derived from acquired magnetic resonance data to control the further performance of the scan, the data acquisition server 412 is programmed to produce such information and convey it to the pulse sequence server 410. For example, during prescans, magnetic resonance data is acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also be employed to process magnetic resonance signals used to detect the arrival of a contrast agent in a magnetic resonance angiography ("MRA") scan. By way of example, the data acquisition server 412 acquires magnetic resonance data and processes it in real-time to produce information that is used to control the scan.

The data processing server 414 receives magnetic resonance data from the data acquisition server 412 and processes it in accordance with instructions downloaded from the operator workstation 402. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 414 are conveyed back to the operator workstation 402 where they are stored. Real-time images are stored in a data base memory cache (not shown in FIG. 4), from which they may be output to operator display 412 or a display 436 that is located near the magnet assembly 424 for use by attending physicians. Batch mode images or selected real time images are stored in a host database on disc storage 438. When such images have been reconstructed and transferred to storage, the data processing server 414 notifies the data store server 416 on the operator workstation 402. The operator workstation 402 may be used by an operator to archive the images, produce films, or send the images via a network to other facilities.

The MRI system 400 may also include one or more networked workstations 442. By way of example, a networked workstation 442 may include a display 444; one or more input devices 446, such as a keyboard and mouse; and a processor 448. The networked workstation 442 may be located within the same facility as the operator workstation 402, or in a different facility, such as a different healthcare institution or clinic.

The networked workstation 442, whether within the same facility or in a different facility as the operator workstation 402, may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may exchanged between the data processing server 414 or the data store server 416 and the networked workstations 442, such that the data or images may be remotely processed by a networked workstation 442. This data may be exchanged in any suitable format, such as in accordance with the transmission control protocol ("TCP"), the internet protocol ("IP"), or other known or suitable protocols.

The above-described systems and methods may be further understood by way of example. This example is offered for illustrative purposes only, and is not intended to limit the scope of the present invention in any way. Various modifications of the invention in addition to those shown and described herein will become apparent to those skilled in the art from the foregoing description and the following examples and fall within the scope of the appended claims.

EXAMPLE

The relationship between cortical lesions ("CLs") and white matter lesions ("WMLs") in multiple sclerosis ("MS") is poorly understood. In addition to their association with disease progression, CLs may also play a role in disease initiation. Thus, it was hypothesized that white matter lesions may be present along tracts directly connected with cortical lesions. As such, an experiment was performed to demonstrate such connectivity, using double inversion recovery ("DIR") images for CL detection coupled with DTI-based probabilistic tractography.

Study participants, which are outlined in Table 1, included patients with relapsing-remitting MS with relative mild disease (EDSS<=4), ages greater than 16. Controls were healthy volunteers without significant neurological diagnosis. Patients were scanned using a 3T GE scanner, and sequences included 3D-MPRAGE, DTI (41 directions) and 3D-DIR. Lesion scoring was performed by two independent raters using a semi-automated lesion scoring of cortical lesions using MRIcron. One rater (rater 2) performed a highly conservative scoring (according to the consensus recommendation). The other rater (rater 1) took a more inclusive approach, including smaller lesions. WM lesions were obtained with consensus, all scored on DIR image, with WV lesions being confirmed with $T_2$ lesion maps.

TABLE 1

Demographic Features of Patient and Control Group

|  | MS (n = 27) | Controls (n-26) |
|---|---|---|
| Age - mean (SD) | 35.9 (13.0) | 38.9 (11.2) |
| Gender ratio (M:F) | 13:14 | N/A |
| Mean EDSS (SD) | 1.17 (0.83) (median 1.0) | N/A |
| Median n lesions (range) | | |
| WML | 34 (3-153) | |
| CL (rater 1 (R1) | 33 (5-82) | |
| CL (rater 2 (R2) | 8 (2-36) | |

MRI Processing

Figure 6:
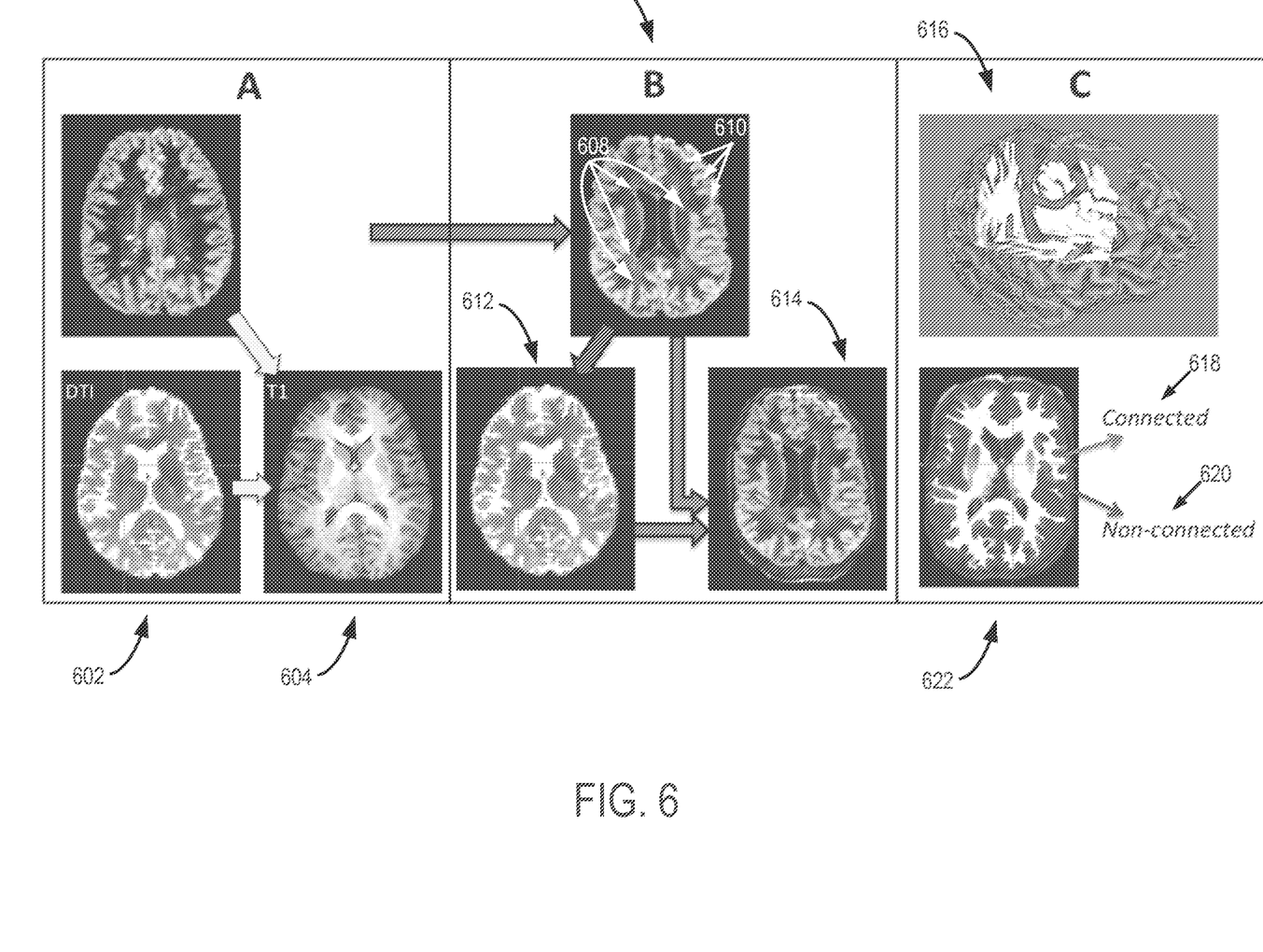
FIG. 6 is a diagram illustrating steps of an example registration and tractography methodology performed in accordance with aspects of the disclosure.

Freesurfer was used for cortical segmentation and FSL5 was used for connectivity analysis and registration, as shown in FIG. 6. Two analyses were performed. The first analysis included analyzing lesion-to-lesion connectivity. Lesion connectivity enumeration was performed using tracts from each individual lesion. Subsequently, the number of WMLs and CLs in each tract (thus seeding from either CL or WML) were identified after binary maps and lesions maps were combined, all encountered connected lesions were counted.

Referring to FIG. 6, an outline is shown with respect to the registration and tractography methodology utilized. Initially, a DIR image 600 and DTI image 602 are registered to a T1 image 604. The DIR image 600 was registered with affine registration, and the DTI image 602 was registered with BBR (boundary based registration) in FSL (FIG. 6A). Lesion maps 606 (top image FIG. 6B; WM lesions 608, cortical GM lesions 610) were drawn on the DIR images and converted to native DTI image space 612. Tractography was performed, seeding from each individual WML and CL and transformed into binary masks in DIR space 614. Subsequently each tract from individual lesions were used to count the number of WML and CL from each individual seed (either WML or CL) and number of connected lesions were calculated from that (example top image 616, FIG. 6C). Binary connected 618 and non-connected 620 cortex maps were created based on cortical segmentation. CL volumes were measured (and corrected for) in both volumes and used for further analysis to calculate this ratio. We report the percentage of lesions that connected from WML to other WML (WML-WML), WML to CL (WML-CL) and CL to WML (CL-WML), outlined in Table 2 and Table 3.

TABLE 2

Table 2: Median Percentage of lesions per person connected from seed to the number of target lesions (e.g., from WM to WM (WML-WML), CLAIM to WML (EL-WML) and WML to CLAIM (WML-CL)

|  | Connectivity | Median percent with ≥1 connection (IQR) | Median percent with ≥2 connections (IQR) | Median percent with ≥3 connections (IQR) |
|---|---|---|---|---|
|  | WML-WML | 79% (68%, 90%) | 57% (35%, 76%) | 40% (13%, 55%) |
| R1 | CL-WML | 50% (39%, 66%) | 19% (13%, 31%) | 11% (2%, 19%) |
|  | WML-CL | 48% (38%, 58%) | 15% (7%, 25%) | 4% (0%, 16%) |

TABLE 2-continued

Table 2: Median Percentage of lesions per person connected from seed to the number of target lesions (e.g., from WM to WM (WML-WML), CLAIM to WML (EL-WML) and WML to CLAIM (WML-CL)

|    | Connectivity | Median percent with ≥1 connection (IQR) | Median percent with ≥2 connections (IQR) | Median percent with ≥3 connections (IQR) |
|----|--------------|-----------------------------------------|------------------------------------------|------------------------------------------|
| R2 | CL-WML       | 50% (31%, 81%)                          | 29% (7%, 53%)                            | 15% (0%, 40%)                            |
|    | WML-CL       | 14% (1%, 27%)                           | 0% (0%, 7%)                              | 0% (0%, 0%)                              |

TABLE 3

Table 3: Number of subjects with seeding lesions connected to minimally 1 target lesion. The number of patients are reported with >0 (any), >35%, >50% and >75% of the seeding lesions connected to any number of target lesions.

|    | Connectivity | N subjects > 0% | N subjects > 25% | N subjects > 50% | N subjects > 75% |
|----|--------------|-----------------|------------------|------------------|------------------|
|    | WML-WML      | 27 (100%)       | 27 (100%)        | 25 (93%)         | 17 (63%)         |
| R1 | CL-WML       | 26 (96%)        | 23 (85%)         | 13 (48%)         | 5 (19%)          |
|    | WML-CL       | 26 (96%)        | 22 (81%)         | 12 (44%)         | 0                |
| R2 | CL-WML       | 25 (93%)        | 21 (78%)         | 13 (48%)         | 9 (33%)          |
|    | WML-CL       | 20 (74%)        | 9 (33%)          | 3 (11%)          | 0                |

Figure 7:
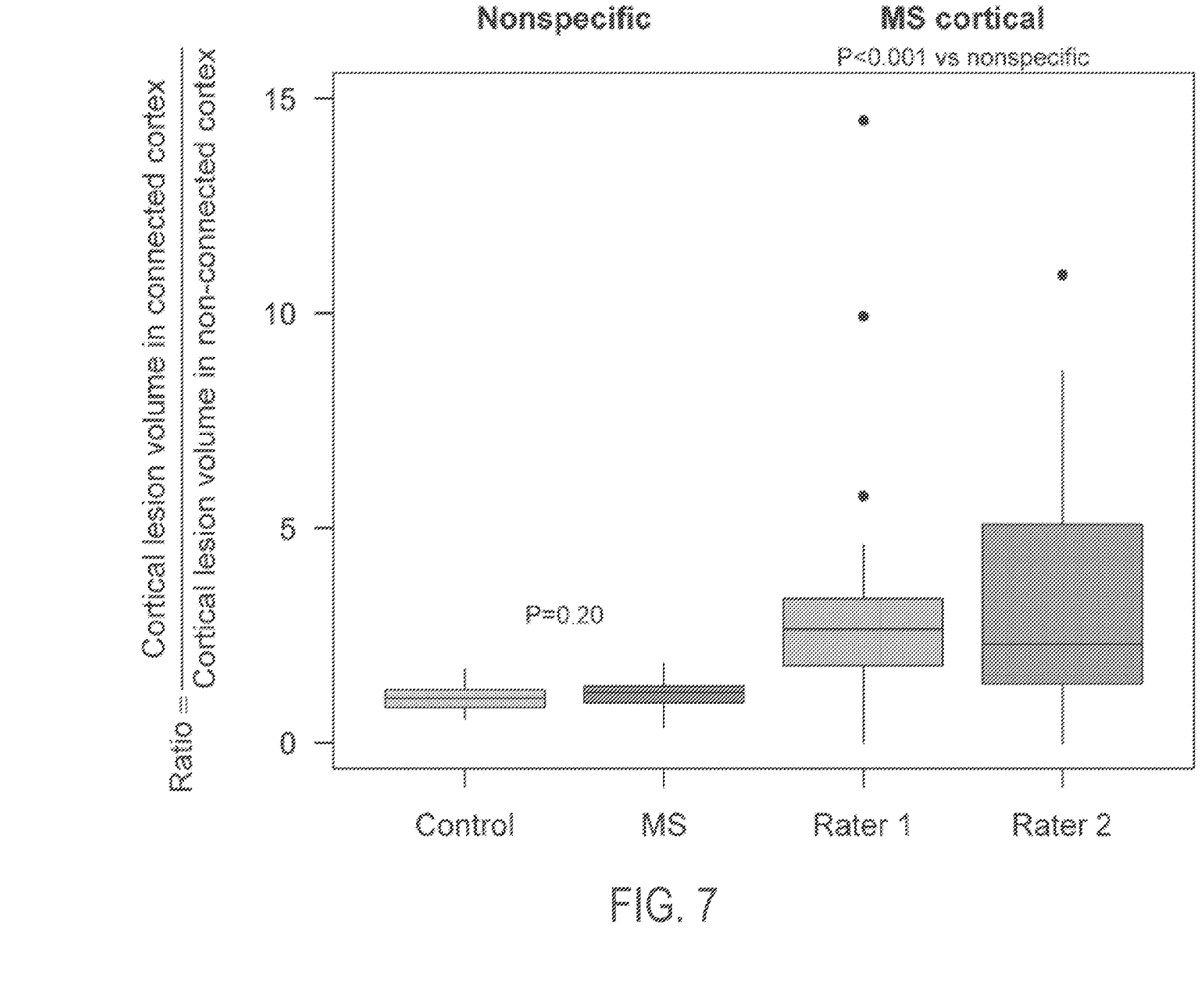
FIG. 7 is a graphical illustration showing ratios of cortical lesions in connected versus non-connected cortex.

The second analysis performed included calculating a ratio of cortical lesions in connected versus non-connected cortex. For this analysis, maps of connected cortex (seeding from each individual WML) were obtained. These connected cortical regions were combined, dividing the entire cortex into "WML connected" and "nonconnected" cortex (FIG. 6C, bottom image 622). The fraction of CLs within connected and non-connected cortex were calculated, correcting for volume. This measurement was quantified as the connected versus non-connected lesion ratio (FIG. 7). Automated cluster analysis was performed to additionally include randomly selected, non-specific DIR cortical hyperintensities in patients and controls. In controls, topographically comparable WM lesion maps were placed in matched controls via affine registration of matched MS lesion maps. Non-parametric Wilcoxon rank-sum/Mann-Whitney U tests were used to compare controls and MS subjects. Wilcoxon signed rank tests were used to evaluate paired differences among MS subjects by lesion type or by rater. Descriptive statistics were used to describe the lesion counts for each MS patient.

Results

Twenty-seven patients (mean age 35.9 (SD 13.0)) and twenty-six controls (mean age 38.9 (SD 11.2)) were included in this example study. Demographics are outlined in Table 1 above.

Lesion to lesion connectivity: Using the cortical lesion maps from two raters (R1 and R2), it was shown that with different cortical lesion scoring relatively similar connectivity analysis results can be obtained. In Table 1, the median fraction of seeding lesions that have target "hits" (with >1, >2 or >3 target hits) is reported. On average, 79% of a subject's WM lesions were connected to at least one other WM lesion. Similarly, in Table 3 the number of patients that have at least one target lesion are reported. In other words, 100% of the patients had at least one WM lesion connected to another WM lesion, and in 17 subjects, greater than 75% of all number of WM lesions were connected to at least one other WM lesion.

Connected versus Non-connected lesion ratios were elevated in MS patients for both rater 1 (median 2.6 [IQR 1.8-3.2]) and rater 2 (median 2.4 [IQR 1.5-5.1]. Comparing these to non-specific cortical hyperintensities in MS patients and controls, this was significantly higher for identified cortical lesions compared to nonspecific cortical areas (median 1.2 [IQR 1.0-1.4]; p<0.001) in MS patients and compared to nonspecific cortical areas in controls (median 1.0 [IQR 0.8-1.2]; p<0.001). These nonspecific cortical areas in MS patients had slightly higher CNCLRs than controls, but did not differ statistically (p=0.20).

In this study, CLs on DIR were 2.5 times as likely to be found in cortex that is connected to WMLs, indicating that CLs and WMLs are topographically related. DIR hyperintensities may be found more frequently in connected cortex, suggesting that some of these less specific appearing regions may also represent poorly visualized CLs due to sensitivity limitations. Similar findings are seen in the descriptive connectivity analysis, where seeding from CLs, 50% of the lesions are connected to at least one WML. These findings are consistent with the hypothesis of CL-WML connectivity.

In summary, compared to "gold standard" histological approaches, conventional in-vivo MRI techniques are lacking sensitivity in detecting critical indicators of multiple sclerosis ("MS") disease. Conventional DIR approaches include the suppression of non-diseased WM and CSF, with sensitivity limitations to subpial plaques, which are present in early, as well as chronic MS disease. However, both deep GM and cortical GM involvement have been shown to have associations with MS-related cognitive changes. Therefore, in recognizing shortcomings of previous approaches, systems and methods are provided herein for producing and utilizing imaging biomarkers indicative of neurological diseases, such as MS, and disease states.

Specifically, a new imaging technique is introduced that, contrary to conventional practice, suppresses healthy GM tissue signals, instead of WM tissue signals, in order to reveal subtle signal changes within the cortex with an increased sensitivity towards cortical lesion detection, thus facilitating enhanced detection of brain lesions associated with early and late of MS.

It is one aspect of the invention to identify and/or utilize biomarkers associated with neurological disease states. For instance, an MRI system may be used to acquire data from a subject by performing a double inversion recovery pulse sequence that selectively nulls magnetic resonance signals originating from gray matter and cerebrospinal fluid. From this data, a set of images is reconstructed and imaging biomarkers may be identified by analyzing the images for specific visual markers or signatures present in regions of interest associated with certain brain tissue, such as white matter tissue. In this manner, neurological disease states and other conditions, including tumor burden or lesion counts, may be determined using identified imaging biomarkers.

It is another aspect of the invention to provide an approach an for quantifying a connectivity between identified lesions, which may have strong implications for MS diagnosis and treatment, with the potential for establishing an understanding of progressive stages of MS disease and at-risk pathways of pathology. In particular, an MRI system may be used to acquire diffusion-weighted data by performing a diffusion-weighted pulse sequence. Then, an image, and/or information, indicative of a connectivity between identified lesions, in accordance with aspects of the disclosure, may be produced using the set of diffusion-weighted images in a probabilistic tractography process. Such generated connectivity information may be used as a biomarker to neurological disease states, disease progressions, tumor burdens, or effects resulting from treatment.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image indicative of a neurological disease state of a subject using a magnetic resonance imaging ("MRI") system, the steps comprising:
    a) directing the MRI system to acquire data by performing a double inversion recovery pulse sequence comprising a first inversion recovery radio frequency ("RF") pulse to selectively null magnetic resonance signals originating from gray matter and a second inversion recovery RF pulse to selectively null magnetic resonance signals originating from cerebrospinal fluid;
    b) directing the MRI system to acquire diffusion-weighted data by performing a diffusion-weighted pulse sequence;
    c) reconstructing a set of images from the data acquired in step a), wherein signals corresponding to gray matter and cerebrospinal fluid are both nulled in the set of images;
    d) reconstructing a set of diffusion-weighted images from the data acquired in step b);
    e) identifying in the set of images reconstructed in step c):
        i) at least one region-of-interest representing at least one cortical lesion;
        ii) at least one region-of-interest representing at least one white matter lesion; and
    f) producing an image indicative of a connectivity between the at least one cortical lesion and the at least one white matter lesion using the set of diffusion-weighted images and the regions-of-interest identified in steps e)i) and e)ii).

2. The method as recited in claim 1, further comprising identifying imaging biomarkers by analyzing the set of images produced in step c) for a visual signature indicative of a lesion in brain tissue.

3. The method as recited in claim 2, wherein the visual signature includes image portions comprising hypointense or hyperintense pixel regions surrounded by hypointense rings.

4. The method as recited in claim 2, wherein the brain tissue comprises white matter tissue.

5. The method as recited in claim 2, further comprising determining a neurological disease state using the identified imaging biomarkers.

6. The method as recited in claim 1, wherein step f) includes performing tractography using the set of diffusion-weighted images reconstructed in step d).

7. The method as recited in claim 6, wherein step f) includes selecting the regions-of-interest identified in steps e)i) and e)ii) as seed points for the tractography.

8. The method as recited in claim 1, further comprising:
    g) directing the MRI system to acquire second data by performing a double inversion recovery pulse sequence that selectively nulls magnetic resonance signals originating from white matter and cerebrospinal fluid;
    h) reconstructing a second set of images from the acquired second data; and
    i) identifying in the second set of images reconstructed in step h):
        i) at least one region-of-interest representing at least one cortical lesion; and
        ii) at least one region-of-interest representing at least one white matter lesion.

9. The method as recited in claim 1, further comprising generating a report indicative of a neurological disease state of the subject based at least in part on the image indicative of connectivity between the at least one cortical lesion and the at least one white matter lesion.

* * * * *